United States Patent
Guan

(10) Patent No.: US 11,413,236 B2
(45) Date of Patent: Aug. 16, 2022

(54) EYELASH LIQUID EYELINER

(71) Applicant: Wengang Guan, Qingdao (CN)

(72) Inventor: Wengang Guan, Qingdao (CN)

(73) Assignee: Qingdao AJLEJSHJ FALSE EYELASH CO., LTD., Shandong (CN)

(*) Notice: Subject to any disclaimer, the term of this patent is extended or adjusted under 35 U.S.C. 154(b) by 45 days.

(21) Appl. No.: 17/137,370

(22) Filed: Dec. 30, 2020

(65) Prior Publication Data
US 2021/0353525 A1 Nov. 18, 2021

(30) Foreign Application Priority Data

May 16, 2020 (CN) .......................... 202010415913.5

(51) Int. Cl.
| A61K 8/89 | (2006.01) |
| A61K 8/25 | (2006.01) |
| A61K 8/34 | (2006.01) |
| A61K 8/73 | (2006.01) |
| A61K 8/81 | (2006.01) |
| A61K 8/92 | (2006.01) |
| A61Q 1/10 | (2006.01) |

(52) U.S. Cl.
CPC ................. *A61K 8/89* (2013.01); *A61K 8/25* (2013.01); *A61K 8/34* (2013.01); *A61K 8/732* (2013.01); *A61K 8/817* (2013.01); *A61K 8/8135* (2013.01); *A61K 8/8147* (2013.01); *A61K 8/922* (2013.01); *A61K 8/927* (2013.01); *A61Q 1/10* (2013.01); *A61K 2800/43* (2013.01)

(58) Field of Classification Search
None
See application file for complete search history.

(56) References Cited

U.S. PATENT DOCUMENTS

2016/0310373 A1* 10/2016 Friel .................... A61K 8/8117

* cited by examiner

Primary Examiner — Ileana Popa
Assistant Examiner — Alissa Prosser

(57) ABSTRACT

The invention discloses an eyelash liquid eyeliner, wherein the raw materials comprise the following components in parts by weight: 50-60 parts of ethyl hexyl acrylate copolymer, 30-40 natural beeswax, 10-12 carnauba wax, 8-12 polyvinylpyrrolidone, 5-7 shellac, 1-3 black talc powder, 20-30 polyvinyl alcohol, 20-30 of silicone resins, 10-12 of codariocalyx motorius saponin extract, 5-7 dual-directional regulation growth promotion factors, 1-3 antifreeze, 1-3 coloring agent, 1-3 preservative, and 5-7 antioxidant. Components in the liquid eyeliner are replaced with natural substances of the natural beeswax, the carnauba wax, the shellac and the like, and the eyelash liquid eyeliner is safe to skin. Besides, organic silicone resins are added, so that the condition that the eyelash liquid eyeliner is broken up when being in contact with water can be effectively avoided, the organic silicone resin can effectively block ultraviolet rays and prevent the ultraviolet rays from destroying roots of eyelashes.

6 Claims, No Drawings

EYELASH LIQUID EYELINER

BACKGROUND OF THE INVENTION

1. Field of the Invention

The invention relates to a cosmetic, in particular to an eyelash liquid eyeliner.

2. Description of the Related Art

In the traditional view, the liquid eyeliner is a prop exclusively for makeup artists. However, as women's understanding and ownership of color cosmetics has deepened, and the requirements for makeup effects have escalated, the liquid eyeliner has also evolved into a "civilian" product with the times. The liquid eyeliner has a strong and smooth line, which is very suitable for the current fashion to pick makeup on the end of the eye; a slight increase in the tail can emphasize the femininity. The user can draw a slightly upward extension line along the arc of the outer corner of the eye, but the upward length should not exceed the width of the double eyelid, it will appear unnatural if too long.

The current liquid eyeliner used on the eyelashes is still based on color, and non-toxic materials are selected for the safety of users. However, applying these substances to the eyelashes for a long time will still have an irreversible effect on the eyelashes.

SUMMARY OF THE INVENTION

The purpose of the invention is to provide an eyelash liquid eyeliner to solve the problems raised in the prior art.

In order to achieve the above purpose, the invention provides the following technical solutions:

an eyelash liquid eyeliner, wherein the raw materials of the eyelash liquid eyeliner comprise the following components in parts by weight: 50-60 parts of ethyl hexyl acrylate copolymer, 20-30 parts of silicone acrylic emulsion, 10-12 parts of starch, 30-40 parts of natural beeswax, 10-12 parts of carnauba wax, 8-12 parts of polyvinylpyrrolidone, 5-7 parts of shellac, 1-3 parts of black talc powder, 20-30 parts of polyvinyl alcohol, 20-30 parts of silicone resins, 10-12 parts of codariocalyx motorius saponin extract, 5-7 parts of dual-directional regulation growth promotion factors, 1-3 parts of antifreeze, 1-3 parts of coloring agent, 1-3 parts of preservative, and 5-7 parts of antioxidant.

An eyelash liquid eyeliner, wherein the raw materials of the eyelash liquid eyeliner comprise the following components in parts by weight: 55 parts of ethyl hexyl acrylate copolymer, 25 parts of silicone acrylic emulsion, 11 parts of starch, 35 parts of natural beeswax, 11 parts of carnauba wax, 10 parts of polyvinylpyrrolidone, 6 parts of shellac, 2 parts of black talc powder, 25 parts of polyvinyl alcohol, 25 parts of silicone resins, 11 parts of codariocalyx motorius saponin extract, 6 parts of dual-directional regulation growth promotion factors, 2 parts of antifreeze, 2 parts of coloring agent, 2 parts of preservative, and 6 parts of antioxidant.

Further, the coloring agent is black iron oxide.

Further, the preservative is any one of ethyl paraben, potassium sorbate, and sodium dehydroacetate.

Further, the antifreeze is any one of methanol, ethanol, isopropanol, ethylene glycol, propylene glycol, and diethylene glycol.

Further, the antioxidant is glutathione and coenzyme Q10.

Further, in the mixing process, the above raw materials are mixed with a centrifuge at high speed to ensure the uniformity of the components, and the mixing temperature is 40-60° C. to ensure that each component has good fluidity.

Compared with the prior art, the advantageous effects of the invention are: components in the liquid eyeliner are replaced with natural substances of the natural beeswax, the carnauba wax, the shellac and the like, and the eyelash liquid eyeliner is safe to skin. The invention also has viscosity, can beautify the eyeliner and adhere false eyelashes at the same time, which is diversified in functions.

Besides, organic silicone resins are added, so that the condition that the eyelash liquid eyeliner is broken up when being in contact with water can be effectively avoided, the organic silicone resin can effectively block ultraviolet rays and prevent the ultraviolet rays from destroying roots of eyelashes, which can effectively protect the eyelashes and prevent the eyelashes from coming off.

DETAILED DESCRIPTION OF THE PREFERRED EMBODIMENTS

The technical solutions in the embodiments of the invention will be clearly and completely described hereinafter with reference to the embodiments of the invention. Obviously, the described embodiments are only a part of the embodiments of the invention, rather than all the embodiments. Based on the embodiments of the invention, all other embodiments obtained by those of ordinary skill in the art without creative efforts shall all fall within the protection scope of the invention.

Embodiment 1

In the embodiment of the invention, an eyelash liquid eyeliner, wherein the raw materials of the eyelash liquid eyeliner comprise the following components in parts by weight: 50 parts of ethyl hexyl acrylate copolymer, 20 parts of silicone acrylic emulsion, 10 parts of starch, 30 parts of natural beeswax, 10 parts of carnauba wax, 8 parts of polyvinylpyrrolidone, 5 parts of shellac, 1 part of black talc powder, 20 parts of polyvinyl alcohol, 20 parts of silicone resins, 10 parts of codariocalyx motorius saponin extract, 5 parts of dual-directional regulation growth promotion factors, 1 part of antifreeze, 1 part of coloring agent, 1 part of preservative, and 5 parts of antioxidant.

In the mixing process, the above raw materials are mixed with a centrifuge at high speed to ensure the uniformity of the components, and the mixing temperature is 40° C. to ensure that each component has good fluidity.

Embodiment 2

In the embodiment of the invention, an eyelash liquid eyeliner, wherein the raw materials of the eyelash liquid eyeliner comprise the following components in parts by weight: 55 parts of ethyl hexyl acrylate copolymer, 25 parts of silicone acrylic emulsion, 11 parts of starch, 35 parts of natural beeswax, 11 parts of carnauba wax, 10 parts of polyvinylpyrrolidone, 6 parts of shellac, 2 parts of black talc powder, 25 parts of polyvinyl alcohol, 25 parts of silicone resins, 11 parts of codariocalyx motorius saponin extract, 6 parts of dual-directional regulation growth promotion factors, 2 parts of antifreeze, 2 parts of coloring agent, 2 parts of preservative, and 6 parts of antioxidant.

In the mixing process, the above raw materials are mixed with a centrifuge at high speed to ensure the uniformity of the components, and the mixing temperature is 50° C. to ensure that each component has good fluidity.

Embodiment 3

In the embodiment of the invention, an eyelash liquid eyeliner, wherein the raw materials of the eyelash liquid eyeliner comprise the following components in parts by weight: 60 parts of ethyl hexyl acrylate copolymer, 30 parts of silicone acrylic emulsion, 12 parts of starch, 40 parts of natural beeswax, 12 parts of carnauba wax, 12 parts of polyvinylpyrrolidone, 7 parts of shellac, 3 parts of black talc powder, 30 parts of polyvinyl alcohol, 30 parts of silicone resins, 12 parts of codariocalyx motorius saponin extract, 7 parts of dual-directional regulation growth promotion factors, 3 parts of antifreeze, 3 parts of coloring agent, 3 parts of preservative, and 7 parts of antioxidant.

In the mixing process, the above raw materials are mixed with a centrifuge at high speed to ensure the uniformity of the components, and the mixing temperature is 60° C. to ensure that each component has good fluidity.

For those skilled in the art, it is obvious that the invention is not limited to the details of the foregoing exemplary embodiments, and the invention can be implemented in other specific forms without departing from the spirit or basic characteristics of the invention. Therefore, regardless of the point of view, the embodiments should be regarded as exemplary and non-limiting. The protection scope of the invention is defined by the appended claims rather than the above description, and therefore it is intended that all modifications falling within the meaning and scope of equivalent elements of the claims are included in the invention.

In addition, it should be understood that although the specification is described in accordance with the embodiments, not every embodiment only includes an independent technical solution. This narrative manner in the specification is only for clarity, and those skilled in the art should regard the specification as a whole; technical solutions in the embodiments can also be appropriately combined to form other implementations that can be understood by those skilled in the art.

The invention claimed is:

1. An eyelash liquid eyeliner, wherein the raw materials of the eyelash liquid eyeliner comprise the following components in parts by weight: 50-60 parts of ethyl hexyl acrylate copolymer, 20-30 parts of silicone acrylic emulsion, 10-12 parts of starch, 30-40 parts of natural beeswax, 10-12 parts of carnauba wax, 8-12 parts of polyvinylpyrrolidone, 5-7 parts of shellac, 1-3 parts of black talc powder, 20-30 parts of polyvinyl alcohol, 20-30 parts of silicone resins, 10-12 parts of codariocalyx motorius saponin extract, 5-7 parts of dual-directional regulation growth promotion factors, 1-3 parts of antifreeze, 1-3 parts of coloring agent, 1-3 parts of preservative, and 5-7 parts of antioxidant.

2. The eyelash liquid eyeliner according to claim 1, wherein the coloring agent is black iron oxide.

3. The eyelash liquid eyeliner according to claim 1, wherein the preservative is any one of ethyl paraben, potassium sorbate, and sodium dehydroacetate.

4. The eyelash liquid eyeliner according to claim 1, wherein the antifreeze is any one of methanol, ethanol, isopropanol, ethylene glycol, propylene glycol, and diethylene glycol.

5. The eyelash liquid eyeliner according to claim 1, wherein the antioxidant is glutathione and coenzyme Q10.

6. The eyelash liquid eyeliner according to claim 1, wherein the preparation method thereof is: put the raw materials of each component into the container of a centrifuge according to the proportion, mix with the centrifuge at high speed to ensure the uniformity of the components, and the mixing temperature is 40-60° C. to ensure that each component has good fluidity.

* * * * *